United States Patent [19]

Lancée et al.

[11] 4,140,107
[45] * Feb. 20, 1979

[54] ECHOSCOPE FOR EXAMINATION OF OBJECTS

[75] Inventors: Charles T. Lancée, Waarder; Gerardus van Zwieten, Smitshoek, both of Netherlands

[73] Assignee: Erasmus University Rotterdam, Rotterdam, Netherlands

[*] Notice: The portion of the term of this patent subsequent to Apr. 12, 1994, has been disclaimed.

[21] Appl. No.: 767,781

[22] Filed: Feb. 11, 1977

Related U.S. Application Data

[63] Continuation-in-part of Ser. No. 587,385, Jun. 16, 1975, Pat. No. 4,016,862, which is a continuation-in-part of Ser. No. 428,769, Dec. 27, 1973, abandoned.

[30] Foreign Application Priority Data

Dec. 28, 1972 [NL] Netherlands ............... 7217703

[51] Int. Cl.² ............................................. A61B 10/00
[52] U.S. Cl. ............................. 128/2 V; 120/2.05 Z; 73/626; 73/900
[58] Field of Search ............ 128/2 V, 2.05 Z, 2.06 B; 330/129, 134

[56] References Cited

U.S. PATENT DOCUMENTS 4,016,862 4/1977 Lancee et al. .................. 128/2 V

Primary Examiner—Robert W. Michell
Assistant Examiner—Francis J. Jaworski
Attorney, Agent, or Firm—Haseltine, Lake & Waters

[57] ABSTRACT

An echoscope for examination of objects with the aid of an ultrasound beam, comprising at least one electro-acoustic element for transmitting and receiving ultrasonic pulses during a transmission-reception period divided into n consecutive time intervals. The ultrasonic pulses are sent to the objects to be examined and are reflected therefrom. The echo signals supplied by the receiving element are amplified by an amplifier with time-dependent gain control. The gain control is brought about by a control voltage generator which supplies a control voltage to said amplifier for determining its signal gain as a function of time. Adjusting means for the control voltage generator are provided to make it possible to change the magnitude of the control voltage in the time intervals as a function of time. The apparatus also comprises a device for visually displaying the echo signals received during each transmission-reception period.

31 Claims, 14 Drawing Figures

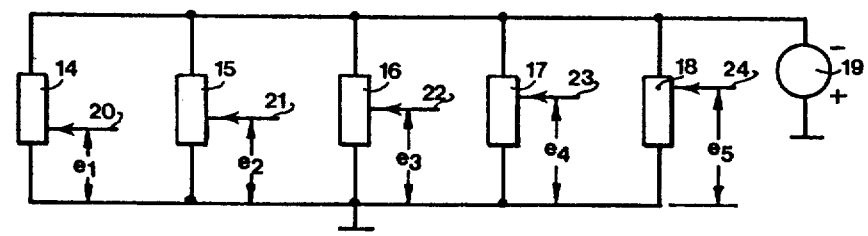
FIG. 10
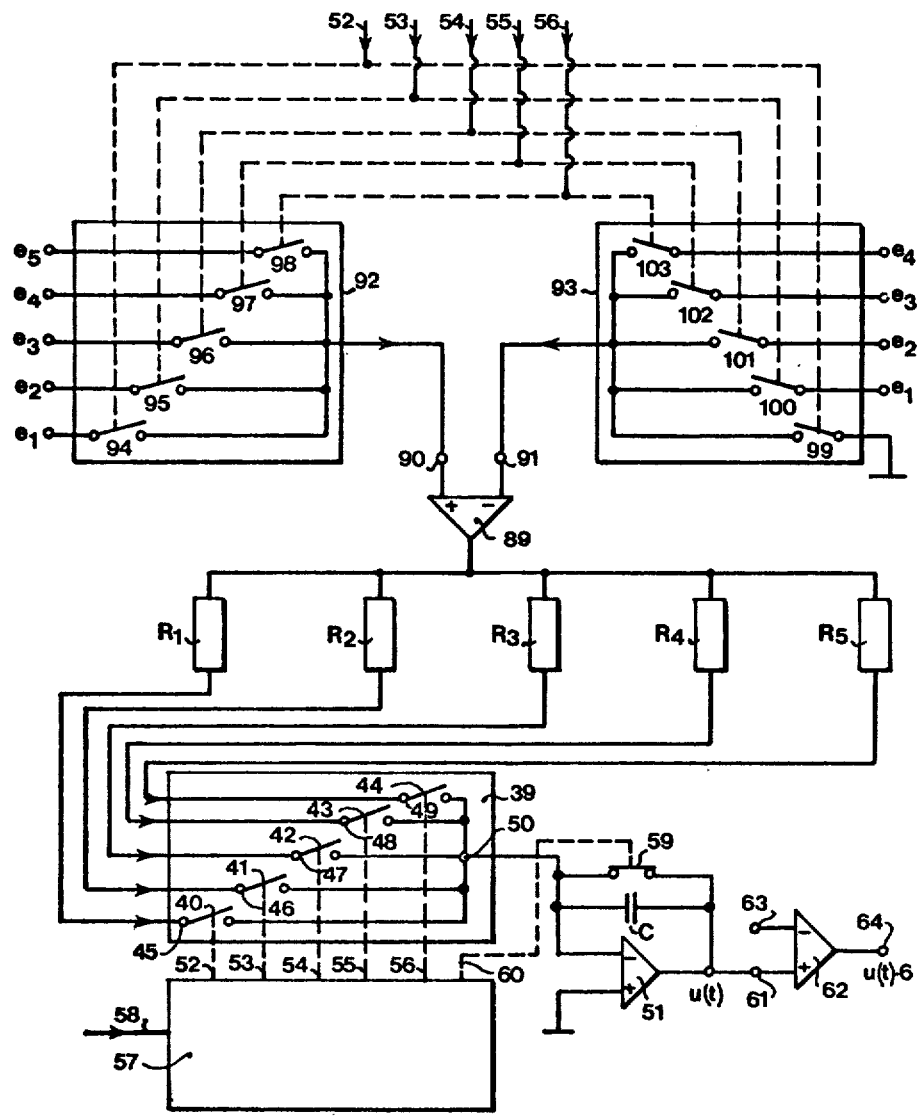

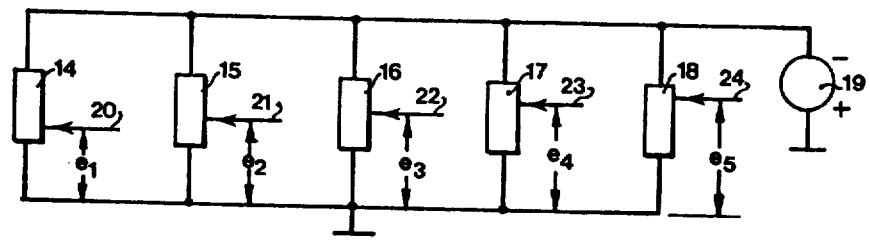
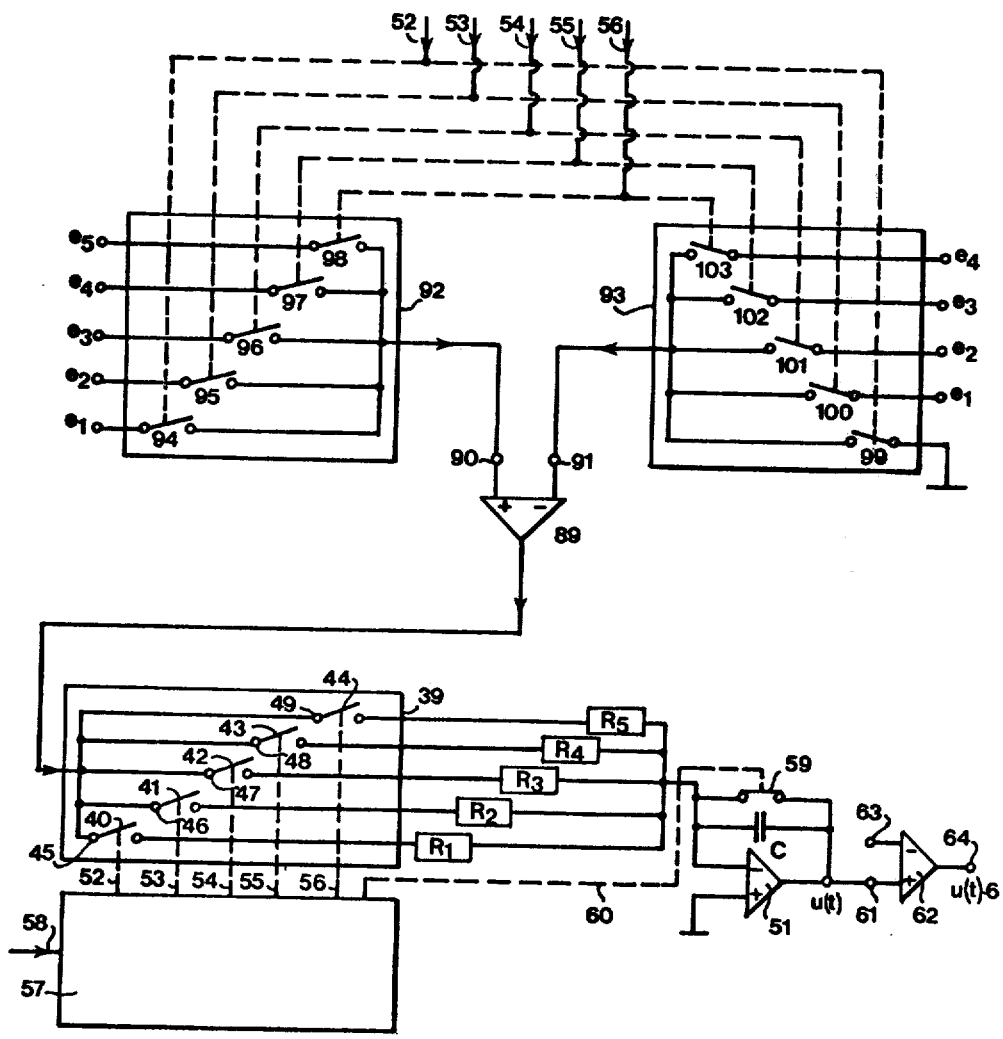
FIG. 11

ECHOSCOPE FOR EXAMINATION OF OBJECTS

BACKGROUND OF THE INVENTION

This application is a continuation-in-part of copending application Ser. No. 587,385 filed June 16, 1975 and now U.S. Pat. No. 4,016,862, which latter is a continuation-in-part of copending application Ser. No. 428,769 filed Dec. 27, 1973, now abandoned.

Ultrasound is used for medical-diagnostic purposes as well as for non-destructive investigation of materials. An ultrasound source intermittently transmits ultrasonic waves of short duration which are directed to the object to be examined. In medical diagnoses, this object may be, for instance, the heart, the eyes, the abdomen or the brains of a patient. Reflection of the ultrasound penetrated into the human body occurs in places where the acoustic impedance is subject to changes, for instance at the interfaces in the tissues. By "acoustic impedance" is to be understood here the product of the density of the object examined, and the velocity of propagation of the ultrasound.

The receiving element converts the reflected waves into an electric echo signal which, after it has been amplified, is displayed on a screen. Within each transmission-reception period echoes are displayed, which taken together form an echogram.

The visual presentation of the echogram can be realized in various ways. When displayed in A-mode, the echoes are presented on a screen as deflections perpendicular to a time axis which indicates the time of reception of the echoes.

When displayed in B-mode, the echo is presented on the screen as a spot whose brightness depends on the strength of the echo signal. As the strength of the echo received to a great extent depends, for instance, on the length and the nature of the path of the sound, it is usually possible to vary the gain with time. In this way, differences in strength of echo signals with different traveling times can be compensated for ("Time gain compensation"). A device for time gain compensation is well-known per se and described for example in Feigenbaum's book "Echocardiography, " Lea and Febiger, Philadelphia 1972, page 21.

With a known echoscope of the type indicated in the above and which is applicable in, for instance, cardiologic examination, a control voltage generator is present for controlling the gain. By means of four dials it is possible to control the gain as a function of time. This will be illustrated with the aid of the graph in FIG. 1. In it the time readings are plotted on the abscissa and the amplification factor on the ordinate.

A first dial is set at the initial gain $G_n$ prevailing during a first time interval 0 to $t_1$ ('near gain') of the transmission-reception period. A second dial is set at the time $t_1$ ('depth compensation'), i.e., the duration of the first time interval.

In a second time interval $t_1$ to $t_2$ the gain varies with time. With a third dial the slope of the gain curve in this interval can be varied between 0 and a positive value ('rate'). Finally, with a fourth dial the gain $G_c$ in the last interval can be set ('coarse gain').

This known echoscope has the disadvantage that the gain, as a function of time, is difficult to control. When for instance with the aid of the first dial the 'near gain' $G_n$ in the first time interval $0-t_1$ is set to a higher or lower value, also the gain curve in the second time interval is shifted upwards or downwards, respectively, and the duration of this second time interval is shortened or lengthened correspondingly. When, for instance, the 'near gain' $G_n$ is reduced the sloping part of the gain curve will come down, as a result of which the second time interval will be increased. This is shown in FIG. 1 with the gain curve indicated with a broken line. But if the gain in the second time interval is to be maintained at the original level, this is only possible by shortening the first time interval with the aid of the second dial.

If, however, the duration of the second time interval is to be maintained, this can be done by increasing the slope $\alpha$ and/or by reducing the 'coarse gain' $G_c$. If the slope $\alpha$ must not be changed, then the original duration of the second time interval can only be maintained by reducing $G_c$.

Changing the 'coarse gain' $G_c$ for instance by decreasing it, will cause the second time interval to be reduced. If this should be undesirable, then the time $t_1$ must be advanced. This is possible by reducing the slope $\alpha$. However, if the slope is to remain the same, then the duration of the second time interval can only be maintained by reducing the 'near gain' $G_n$.

In the way described above, the duration of the second time interval is reduced to its original value, but its position along the time axis has been shifted. The times $t_1$ and $t_2$ are advanced to the same extent. If both the position and the duration of the second time interval are to be maintained, as will generally be necessary, this can be effected only by bringing the entire gain curve to a lower level.

The same problems are met if $t_1$ and $\alpha$ are to be changed. In diagnostic examination the most suitable gain curve must always be re-adapted to each individual case, so that all four setting parameters ($G_n$, $t_1$, $\alpha$ and $G_c$) may be changed. It is evident that finding the correct setting will then be very difficult.

Furthermore, a device is known for generating a voltage as an arbitrary function of time. The function is approximated by a staircase wave form by sequentially connecting a number of precision resistors to a reference voltage. The staircase waveform is integrated to produce a linear segment curve (H. Schmid: "Sequential analog-digital computer," Proc. of the fall joint computer conference, Las Vegas, Nev., November 1965, chapter "arbitrary function generation," pp. 915-928). However, for each function to be generated a different set of resistors is needed.

From U.S. Pat. No. 3,033,029 an echograph for ultrasonic inspection of objects in A-mode is known which comprises an amplifier and a gain compensator to produce a substantially constant echo signal throughout the distance traversed by the ultrasound in the object. To that end for any given object to be tested the characteristic curve of the received signal amplitude is determined as a function of the distance traveled by the ultrasonic pulse. Thereafter a voltage in staircase waveform is generated and after integration of this voltage it is applied to a gain control circuit. Voltage output variations which are a function of penetration depth are thereby eliminated.

With this known echograph it is only possible to vary the slope of the gain curve in a certain time interval by the adjustment of a set of new voltages which produce a staircase waveform approximating the desired slope. This change of slope, even in one single time interval, requires readjustment of more than one parameter.

The echoscope indicated in the abstract shows the improvement of the control voltage generator comprising a. at least two adjustable voltage sources, each of which cooperates with the adjusting means for arbitrarily setting the voltages ($e_i$, $e_j$) of said sources prevailing at the corresponding interval points of time ($t_i$ and $t_j$ respectively) between a minimum and a maximum value;

b. at least one differential amplifier co-operating with the adjustable voltage sources for providing a difference voltage ($a_j \cdot e_j - b_j \cdot e_i$) during a time interval $t_i$ to $t_j$, $a_j$ and $b_j$ being multiplication factors representing a possible attenuation or amplification of the voltages ($e_i$, $e_j$) before their being supplied to the differential amplifier;

c. integrator means for supplying the control voltage to the echo signal amplifier, said integrator means cooperating with the differential amplifier to integrate the difference voltage ($a_j \cdot e_j - b_j \cdot e_i$) during the respective time interval ($t_j$ to $t_i$) with an integrator time constant $(RC)_j$; and d. switching means co-operating with said integrator means for successively integrating the difference voltages ($a_j \cdot e_j - b_j \cdot e_i$) during consecutive time intervals ($t_j - t_i$), said time intervals ($t_j - t_i$) corresponding to the respective integrator time constants $(RC)_j$ according to the relation $$b_k \cdot \frac{t_k - t_j}{(RC)_k} = a_j \cdot \frac{t_j - t_i}{(RC)_j}$$

with $i = 0, 1, 2, \ldots, n-1$ $j = +1$, and $k = j + 1$, but $k \leq n$.

By "electro-acoustic element" is meant an element which may convert an electric signal into an acoustic signal of ultrasonic frequency and vice versa. By "at least one electro-acoustic element" is meant that there is either at least a single element for both transmission and reception or at least one element for transmission and one for reception.

Instead of the four parameters mentioned above, viz. $G_n$, $t_1$, $\alpha$ and $G_c$ the present invention provides, as setting parameters, the gains at at least two different interval points of time. As a result, the setting of the gain curve desired becomes more flexible and more direct, i.e., a wider choice of curve shape is possible, and the inter-dependence of the setting parameters will be smaller than with the known echoscope. This also leads to a simpler and more rapid setting of the desired gain curve.

Changing the gain at one of the interval points of time will only influence the gain curve in the two consecutive time intervals separated by the respective interval point of time. Outside these intervals the gain curve remains unchanged.

Choosing two successive interval points of time for varying the gain will allow influencing the gain curve in not more than three consecutive time intervals.

Choosing two non-successive interval points of time for varying the gain will allow influencing the gain curve in not more than four time intervals.

Not only the gain at various interval points of time but also these times themselves may be variable.

The invention will be elucidated with reference to the embodiment illustrated in the accompanying drawing.

BRIEF DESCRIPTION OF THE DRAWING

FIGS. 7–14 show variant embodiments of the control voltage generator according to FIG. 2.

DESCRIPTION OF PREFERRED EMBODIMENTS

Figure 6:
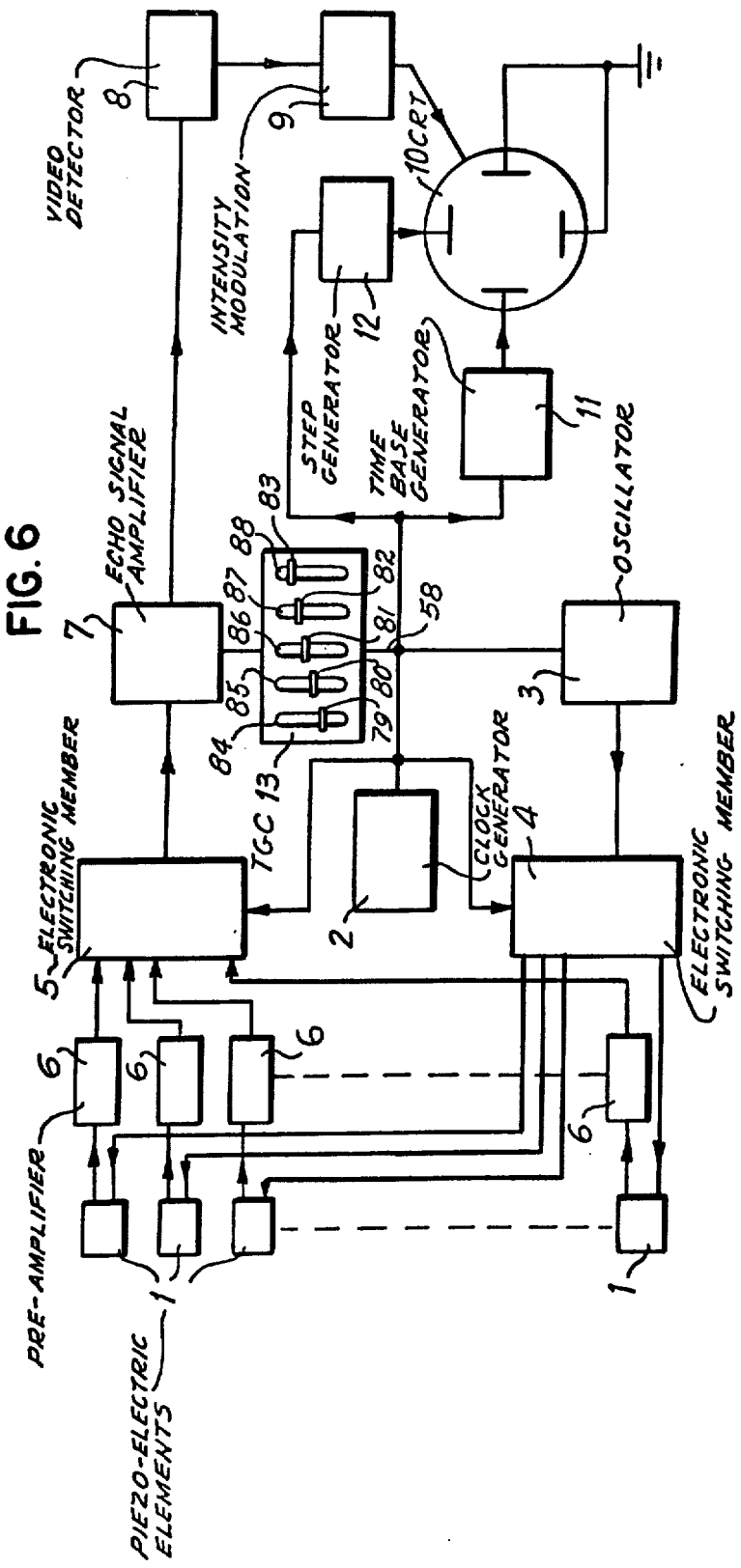
FIG. 6 schematically shows an echoscope according to the present invention for diagnostic purposes.

FIG. 6 shows an echoscope with B-mode display for obtaining a real-time cross-sectional image of a biological structure such as the heart. It is to be understood, however, that although this is an important application of the invention, its use is not limited to such application. For example, the invention may also be used for echoscopes with A-mode display.

FIG. 6 shows a number of pieze-electric elements 1 arranged in a row. The elements 1 are supported in a transducer of which the acoustically active surface is to be placed on the body of a patient to be examined. By the acoustically active surface is meant the surface which transfers the ultrasonic vibrations of the elements to the patient's body.

Each of the elements 1 serve as transmitter and receiver of ultrasound. The ultrasound pulses emitted by a certain element are reflected at the interfaces in the tissues. The reflected ultrasound is converted into an electric echo signal to be displayed on a cathode ray tube.

The elements 1 have parallel axes of radiation lying in a plane adapted to intersect the body part being examined along a predetermined cross-section. The elements are repeatedly excited at such a high repetition frequency that an instantaneous two-dimensional image of said cross-section is observed on the screen of the cathode ray tube.

A more detailed description of such an echoscope is found in U.S. Pat. No. 3,789,833.

The excitation of the piezo-electric elements is controlled by a clock generator 2 which also controls an oscillator 3 and electronic switching members 4 and 5. The electronic switching member 4 successively connects all piezo-electric elements 1 to the oscillator 3 which generates the oscillations for the excitation of the elements.

Each element 1 is connected to a pre-amplifier 6 which amplifies the echo signals obtained upon reception of reflected ultrasound. The outputs of the pre-amplifiers 6 are, through the intermediary of the electronic switching member 5, successively connected to a common echo signal amplifier 7. The gain of amplifier 7 is determined by a time-gain compensating means 13 which is also under the control of clock generator 2. The amplified echo signals are then supplied to a video detector 8 and a device 9 for producing an intensity modulation of the cathode ray by means of the intensity-control electrode of the cathode ray tube 10.

The clock generator 2 also controls a time base generator 11 and a step generator 12 which are connected to the horizontal and vertical deflecting plates of cathode ray tube 10 respectively. As more fully described in U.S. Pat. No. 3,789,833, the echo signals originating from a particular cross-section of the body are displayed on the cathode ray tube screen in a coordinate system wherein one coordinate represents the position of the emitted ultrasound beam, and another coordinate represents the time of reception of the echo signals.

Figure 2:
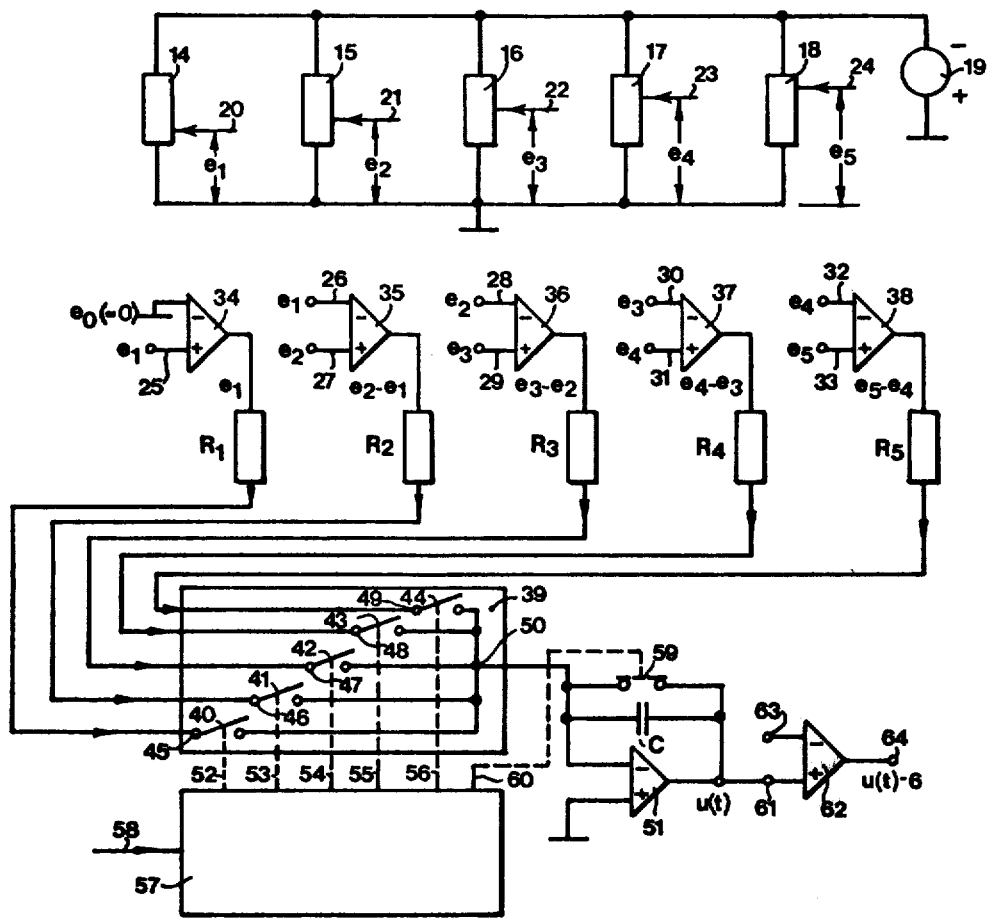
FIG. 2 is a diagrammatic representation of a control voltage generator for an amplifier according to the invention.

The time-gain compensating means 13 comprises a control voltage generator which is shown in more detail in FIG. 2.

In FIG. 2 the numerals 14 to 18 refer to a number of sliding potentiometers which are connected to a source 19 supplying a d.c. voltages which, if necessary, may be adjustable. It is supposed that in this case source 19 supplies a voltage of 6V. The sliding contacts 20 to 24 of the sliding potentiometers are connected to the inputs 25 to 33 of differential amplifiers 34 to 38. The outputs of the differential amplifiers are connected to a schematically shown switching unit 39 through resistors $R_1$ to $R_5$. Switching unit 39 contains a number of switches 40–44. Their contacts 45–49 are connected to resistors $R_1$ to $R_5$. The remaining contacts are connected to a common terminal 50, which is connected to an integrator 51 with capacitor C. Switches 40–44 are semi-conductor switches which, as schematically indicated by dash lines 52–56, are controlled by a timing generator 57. During each transmission-reception period timing generator 57 produces a sequence of timing signals which initiate switches 40–44 to close at the interval points of time. Switch 40 connects the integrator 51 to the contact 45 during a first interval 0 to $t_1$ of the transmission-reception period; during a subsequent second interval $t_1$ to $t_2$ it is connected to the resistor $R_2$; during a third interval $t_2$ to $t_3$ it is connected to resistor $R_3$; during a fourth interval $t_3$ to $t_4$ it is connected to resistor $R_4$ and during a fifth interval $t_4$ to $t_5$ it is connected to resistor $R_5$. In closed state switches 40–44 have internal resistances which are negligible with respect to the resistance of resistors $R_1$ to $R_5$.

Timing generator 57 is connected to clock generator 2 through lead 58, as shown in FIG. 6. Each time the clock generator 2 starts a new transmission-reception period, timing generator 57 initiates switching unit 39 to connect integrator 51 to contact 45. For timing generator 57 any timing generator may be used capable of sequentially supplying timing signals at the interval points of time. The instants at which the timing signals are supplied should preferably be variable. For example, FIG. 4 of the above-cited article of H. Schmid shows a control unit with a timing generator and a switching unit of the kind which may be applied to the control voltage generator of FIG. 2 of the present application.

Timing generator 57 may also be made up of an m-bit counter connected to a code converter (decoder) which supplies the required timing signals at the interval points of time to close switches 40–44 through appropriate switch drivers. Other timing generators are conceivable, e.g., one using a sawtooth voltage generator connected to an analog decoder consisting of n comparators, one for each of the interval points of time $t_1, t_2, \ldots, t_i, t_j, t_k, \ldots, t_n$. The output signals of the comparators are supplied to the switching unit in order that at the appropriate instants the latter may be switched over to another differential amplifier. By varying the slope of the sawtooth voltage, the switchover instants can easily be varied.

Parallel to the capacitor C is a switch 59. It is also under control of timing generator 57, as schematically indicated by the dash line 60. The output voltage u(t) of the integrator 51 is applied to the input 61 of a differential amplifier 62. To the other input 63 of the amplifier, a voltage of +6 Volts is applied. The voltage at the output 64 of the differential amplifier 62 will then be $C(t) = u(t) - 6$ Volts.

Figure 1:
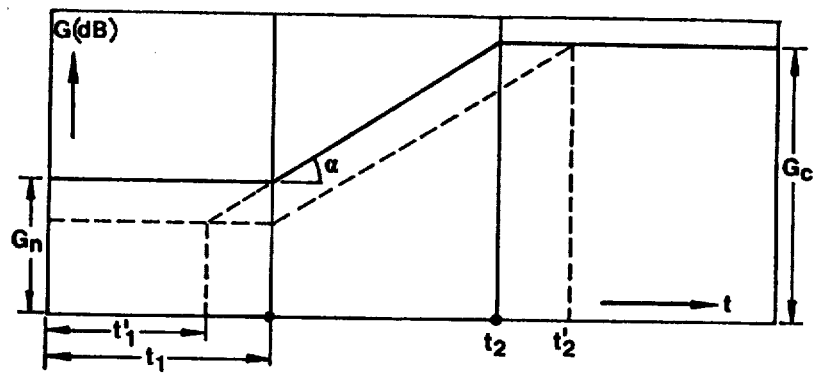
FIG. 1 shows a gain curve of a known echoscope.
Figure 3:
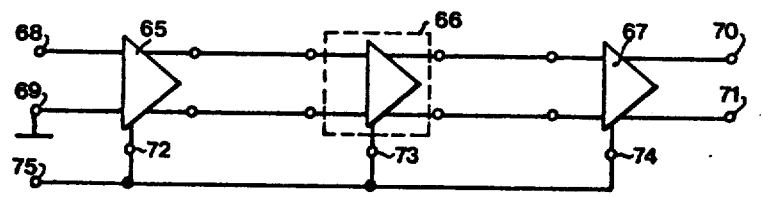
FIG. 3 is a schematic diagram of a three-stage echo signal amplifier for an apparatus according to the invention.

The output 64 is connected to the echo signal amplifier 7 of FIG. 6. This amplifier is schematically represented in FIG. 3 and consists of three identical amplifier stages 65, 66 and 67. The echo signals are fed to the inputs 68, 69 and arrive amplified at the outputs 70, 71 which are connected to a video detector 8 shown in FIG. 6. The amplifier stages 65 to 67 are provided with contacts 72, 73 and 74, respectively, through which the gain may be set. The contacts 72 to 74 are centrally connected at 75 to the output 64 of the control voltage generator represented in FIG. 2.

The three amplifiers 65 to 67 are constructed as an integrated circuit of the S 5733 type of Signetics Corporation, as described in their Preliminary Specification of August 1969.

The differential amplifier here is a wideband video amplifier with differential output. This amplifier can be connected to an external resistor for setting the gain.

Figure 4:
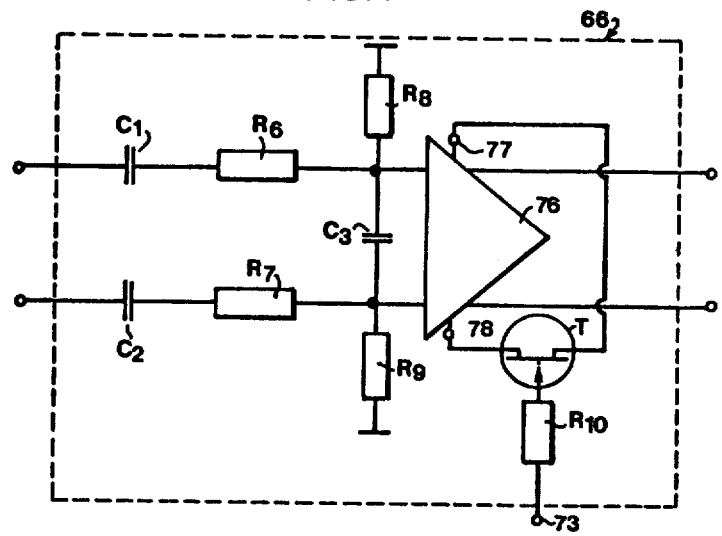
FIG. 4 represents a detail of the amplifier shown in FIG. 3.

FIG. 4 further illustrates the middle amplifier stage 66. The actual amplifier, of the S 5733 type, is referred to by the numeral 76. Its gain can be varied in the range of 10 to 400.

In order that a minimum gain of 1 may be obtained, a 10-fold attenuation must be applied. This attenuation is realized by means of a band-pass filter for each amplifier stage. With this, it is also possible to limit the noise. For this purpose the differential amplifier 76 has at its input a symmetrical band-pass filter consisting of the resistors $R_6$ to $R_9$ and the capacitors $C_1$ to $C_3$.

Suitable values are: $R_6 = R_7 = 910\Omega$; $C_1 = C_2 = 150$ pF and $C_3 = 82$ pF.

Connected between the control inputs 77 and 78 (gain select pins) of the differential amplifier 76, is a variable electronic resistor in the form of a field-effect transistor T of the U 1898 E type made by Amelco Semiconductor, U.S.A.

The control electrode of T is connected to the control input 73 through the resistor $R_{10}$ having a value of 13$\Omega$. This connection results in a gain range of 1 to 21.5 times per stage.

The control voltage generator described above operates as follows: The sliding potentiometers 14 to 18 are set in accordance with the desired gain curve. Together with the voltage source 19, they each form a voltage source, with the respective voltages indicated by $e_1, e_2, e_3, e_4$ and $e_5$. Consequently, the output voltages of the differential amplifiers 34 to 38 are $e_1$; $e_2 - e_1$; $e_3 - e_2$; $e_4 - e_3$; and $e_5 - e_4$, respectively. More generally, the output voltage of differential amplifier 34 is $e_1 - e_0$, in which $e_0$ need not necessarily be zero.

The capacitor C and the resistors $R_1$ to $R_5$ are chosen so that:

$$R_1C = t_1 \\ R_2C = t_2 - t_1 \\ R_3C = t_3 - t_2 \\ R_4C = t_4 - t_3 \\ R_5C = t_5 - t_4 \tag{1}$$

Initially, all switches in switching unit 39 are in the open position indicated in FIG. 2 and the switch 59 is closed, so that the output voltage of the integrator is zero.

At the start of the transmission-reception period ($t = 0$), the switch 59 is opened and the switching unit 39 will under the control of timing generator 57 connect the central contact 50 with the contact 45. As a result, the integrator 51 is set into operation for a first time interval 0 to $t_1$ of 12.5 μsec.

Therefore, the output voltage u(t) of the integrator is:

$$u(t) = \frac{-1}{R_1 C} \int_0^t e_1 dt \text{ for } 0 \leq t \leq t_1, \quad (2)$$

so that $u(t_1) = -e_1$, with $R_1 C = t_1 = 12.5$ μsec.

At time $t = t_1 = 12.5$ μsec., the switching unit 39 connects the integrator 51 to the contact 46. The variation in the output voltage of the integrator in the interval $t_1$ to $t_2$ ($t_2 = 25$ μsec) is then given by $$u(t) = \frac{-1}{R_2 C} \int_{t_1}^t (e_2 - e_1) dt - e_1 \text{ for } t_1 \leq t \leq t_2 \quad (3)$$

so that $u(t_2) = -e_2$, with $R_2 C = t_2 - t_1 = 12.5$ μsec.

Likewise, the integrator 51 is via the contacts 47, 48 and 49 connected to the differential amplifiers 36, 37 and 38 at the times $t_3 = 50$ μsec., $t_4 = 100$ μsec., and $t_5 = 200$ μsec.

For the following time intervals $t_2$ to $t_3$, $t_3$ to $t_4$ and $t_4$ to $t_5$ one may write:

$$u(t) = \frac{-1}{R_3 C} \int_{t_2}^t (e_3 - e_2) dt - e_2 \text{ for } t_2 \leq t \leq t_3 \quad (4)$$

so that $u(t_3) = -e_3$, with $R_3 C = t_3 - t_2 = 25$ μsec;

$$u(t) = \frac{-1}{R_4 C} \int_{t_3}^t (e_4 - e_3) dt - e_3 \text{ for } t_3 \leq t \leq t_4 \quad (5)$$

so that $u(t_4) = -e_4$, with $R_4 C = t_4 - t_3 = 50$ μsec; and $$u(t) = \frac{-1}{R_5 C} \int_{t_4}^t (e_5 - e_4) dt - e_4 \text{ for } t_4 \leq t \leq t_5, \quad (6)$$

so that $u(t_5) = -e_5$, with $R_5 C = t_5 - t_4 = 100$ μsec.

Note that all voltages u(t) at the interval points of time $t_1, t_2, t_3, t_4$ and $t_5$ are only dependent on the setting of the respective potentiometer. For example, the voltage $u(t_3)$ only depends on the setting of potentiometer 16 and remains unchanged in the case of a variation in the adjustment of the other potentiometers 20, 21, 23 and 24.

In the embodiment of FIG. 2 a necessary and sufficient condition for the adjustment of any of the voltages $u(t_i)$ being only dependent on the settings of the corresponding i-th potentiometer, is given by the relation $$\frac{t_5 - t_4}{R_5 C} = \frac{t_4 - t_3}{R_4 C} = \frac{t_3 - t_2}{R_3 C} = \frac{t_2 - t_1}{R_2 C} = \frac{t_1}{R_1 C} \quad (7)$$

This condition is certainly satisfied by choosing the capacitor C and the resistors $R_1$ to $R_5$ according to relation (1).

For each of the five time intervals the respective control voltage follows from $$C(t) = u(t) - 6 \text{ Volts.}$$

The control voltage C (t) is applied to the control inputs 72 to 74 of the amplifiers 65 to 67 through the contact 75 (see FIG. 3). As the voltage u(t) of the integrator 51 may range between 0 and 6 Volts, the control voltage C (t) varies between $C_{min.} = -6$ V, and $C_{max.} = 0$V. Within a large part of this last mentioned range the gain (in dB) increases substantially in direct proportion to the control voltage.

Figure 5:
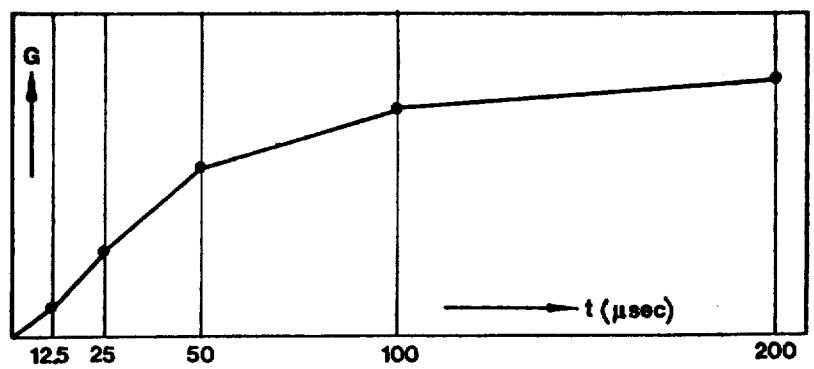
FIG. 5 illustrates a gain curve obtained with the apparatus according to the invention.

FIG. 5 shows a gain curve as obtained with the settings shown in FIG. 2 for the sliding potentiometers 14 to 18. On the abscissa are plotted the time readings, with $t = 0$ indicating the beginning of a transmission-reception period. In FIG. 6 the sliding potentiometers of the time-gain compensating means 13 are shown by their adjusting knobs 79, 80, 81, 82 and 83. These knobs are slidable in vertical slits 84–88 provided in the front panel of the echo scope.

FIG. 5 shows that the settings of the sliding potentiometers 14–18 in FIG. 2 and FIG. 6 give a visual presentation of the shape of the gain curve, thus facilitating the task of the operator. He can immediately observe the effect produced on the gain curve of a variation in the setting, so that this curve need not be displayed on a CRT screen.

Although in FIG. 5 the gains at all five interval points of time are between the same minimum (0 dB) and maximum gain (80 dB), this is not essential. It is also conceivable that the gain at each interval point of time can be between a respective minimum and maximum value.

It will be clear that with the above-described echoscope not only a gain curve wth a positive slope α can be realized, but also a curve with one or more parts of it having a negative slope.

With the circuit shown in FIG. 4 an extremely rapid change in gain may be effected. Thus it is possible wth an adapted control voltage to have the total gain of the three-stage amplifier shown in the FIGS. 3 and 4 changed from the minimum (1×) gain to the maximum 10,000 ($21.5^3$) gain, i.e., from 0 to 80 dB, within 5 μsec.

Due to this high speed, which can be realized with the aid of a variable electronic resistor such as a field-effect transistor, it is possible to use the invention also for very short transmission-reception periods. This is of particular advantage if the ultrasound is to cover only a short distance, as is the case with ultrasound examination of the eye.

DESCRIPTION OF VARIANT EMBODIMENTS

FIGS. 7–14 show a number of variant embodiments of the control voltage generator of FIG. 2.

Whereas in the control voltage generator of FIG. 2 the voltages $e_1$ to $e_5$ are directly supplied to the inputs of the differential amplifiers 34 to 38, these voltages may also be attenuated or amplified according to a certain multiplication factor. In the case of an attenuation this may be realized by means of additional voltage dividers shown in the embodiment of FIG. 7. In that case the voltages $e_1$, $e_2$, $e_3$ etc., are not directly supplied to the corresponding inputs 25, 27, 29 etc. of the differential amplifiers, but via voltage dividers $R_2/r_1$; $R_0/r_2$ and $R_0/r_2'$; $R_0/r_3$ and $R_0/r_3'$ etc.

Putting $$\frac{R_0}{R_0 + r_1} = a_1 \qquad \frac{R_0}{R_0 + r_2'} = b_2 \qquad (8)$$

$$\frac{R_0}{R_0 + r_2} = a_2 \qquad \frac{R_0}{R_0 + r_3'} = b_3$$

$$\frac{R_0}{R_0 + r_3} = a_3 \qquad \frac{R_0}{R_0 + r_4'} = b_4$$

$$\frac{R_0}{R_0 + r_4} = a_4 \qquad \frac{R_0}{R_0 + r_5'} = b_5$$

$$\frac{R_0}{R_0 + r_5} = a_5$$

it follows in general that the voltage $u(t_j)$ after integration of the output voltage of the j-th differential amplifier is $$u(t_j) = \frac{-1}{R_j C} \int_{t_i}^{t_j} (a_j \cdot e_j - b_j \cdot e_i) dt + u(t_i) \qquad (9)$$

or $$u(t_j) = \frac{-(t_j - t_i)}{R_j \cdot C} \cdot (a_j \cdot e_j - b_j \cdot e_i) + u(t_i)$$

For example, $$u(t_1) = \frac{-t_1}{R_1 C} \cdot a_1 e_1 \qquad (10)$$

and $$u(t_2) = \frac{-(t_2 - t_1)}{R_2 C} \cdot (a_2 \cdot e_2 - b_2 \cdot e_1) - \frac{t_1}{R_1 C} \cdot a_1 \cdot e_1 \qquad (11)$$

In order that $u(t_2)$ is only dependent on the setting of potentiometer 15, the following relation must be satisfied $$b_2 \cdot \frac{t_2 - t_1}{R_2 C} = a_1 \cdot \frac{t_1}{R_1 C} \qquad (12)$$

From (11) and (12) it follows that $$u(t_2) = \frac{-(t_2 - t_1)}{R_2 C} \cdot a_2 \cdot e_2 \qquad (13)$$

Likewise, for $u(t_3)$ being only dependent on the setting of potentiometer 16, the condition $$b_3 \cdot \frac{t_3 - t_2}{R_3 C} = a_2 \cdot \frac{t_2 - t_1}{R_2 C} \qquad (14)$$

must be satisfied, in which case $$u(t_3) = \frac{-(t_3 - t_2)}{R_3 C} \cdot a_3 \cdot e_3 \qquad (15)$$

Conditions (12) and (14) may in general be written as follows $$b_k \cdot \frac{t_k - t_j}{R_k C} = a_j \cdot \frac{t_j - t_i}{R_j C} \qquad (16)$$

With $i = 0, 1, 2, \ldots, n-1$ $j = i+1$ and $k = j+1$, but $k \leq n$ where n is the number of time intervals.

The voltages $u(t_j)$ may be made independent of the duration of the time intervals $t_j - t_i$ by choosing them proportional to the corresponding integration time constants $R_j C$, $$\frac{t_j - t_i}{R_j C} = c_j \qquad (17)$$

In the special case where the proportionality factor c is 1, i.e., $$\begin{aligned} t_1 &= R_1 C \\ t_2 - t_1 &= R_2 C \\ t_3 - t_2 &= R_3 C \\ t_4 - t_3 &= R_4 C \\ t_5 - t_4 &= R_5 C \end{aligned} \qquad (18)$$

the voltages $u(t_j)$ are $$\begin{aligned} u(t_1) &= -a_1 \cdot e_1 \\ u(t_2) &= -a_2 \cdot e_2 \\ u(t_3) &= -a_3 \cdot e_3 \\ u(t_4) &= -a_4 \cdot e_4 \text{ and} \\ u(t_5) &= -a_5 \cdot e_5 \end{aligned} \qquad (19)$$

In that case it follows from (16) that the following equation must be satisfied $$b_k = a_j \qquad (20)$$

or $$\begin{aligned} r_2' &= r_1 \\ r_3' &= r_2 \\ r_4' &= r_3 \text{ and} \\ r_5' &= r_4 \end{aligned} \qquad (21)$$

Figure 8:
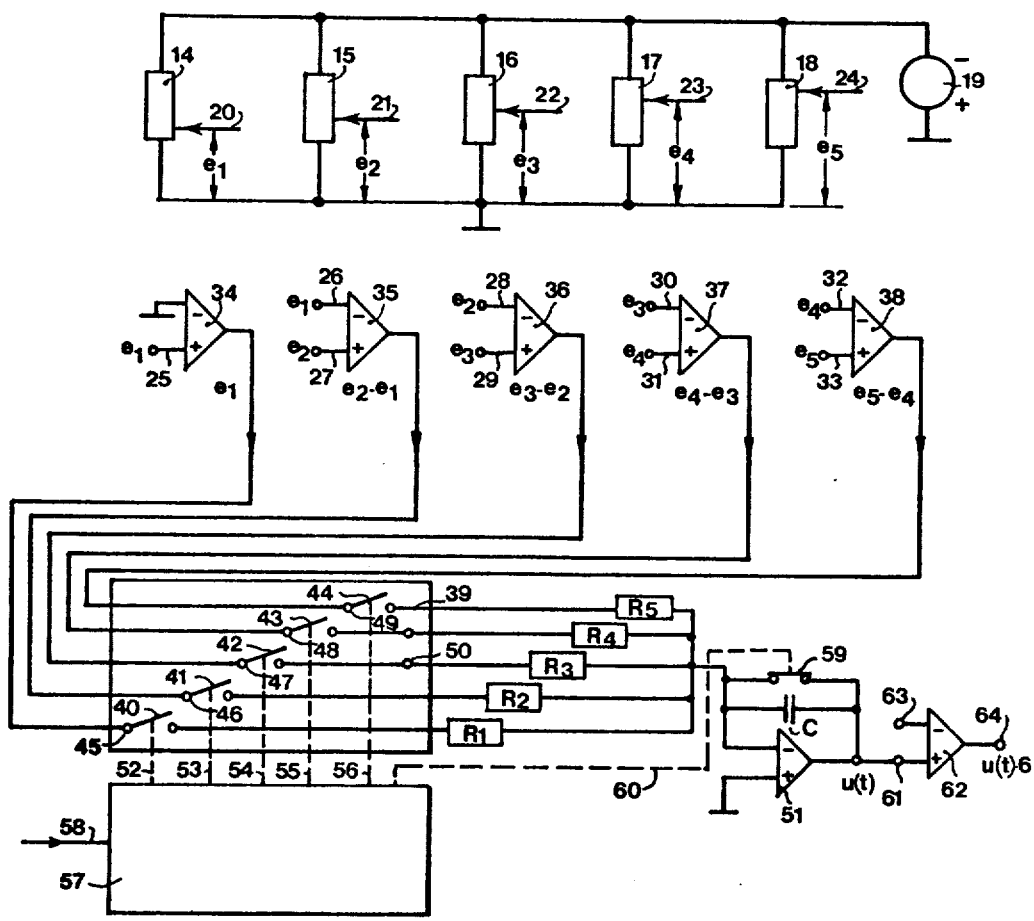

The embodiment according to FIG. 8 only differs from the one according to FIG. 2 in that the switching unit 39 and the integrator are interconnected via the resistors $R_1$ to $R_5$.

Figure 7:
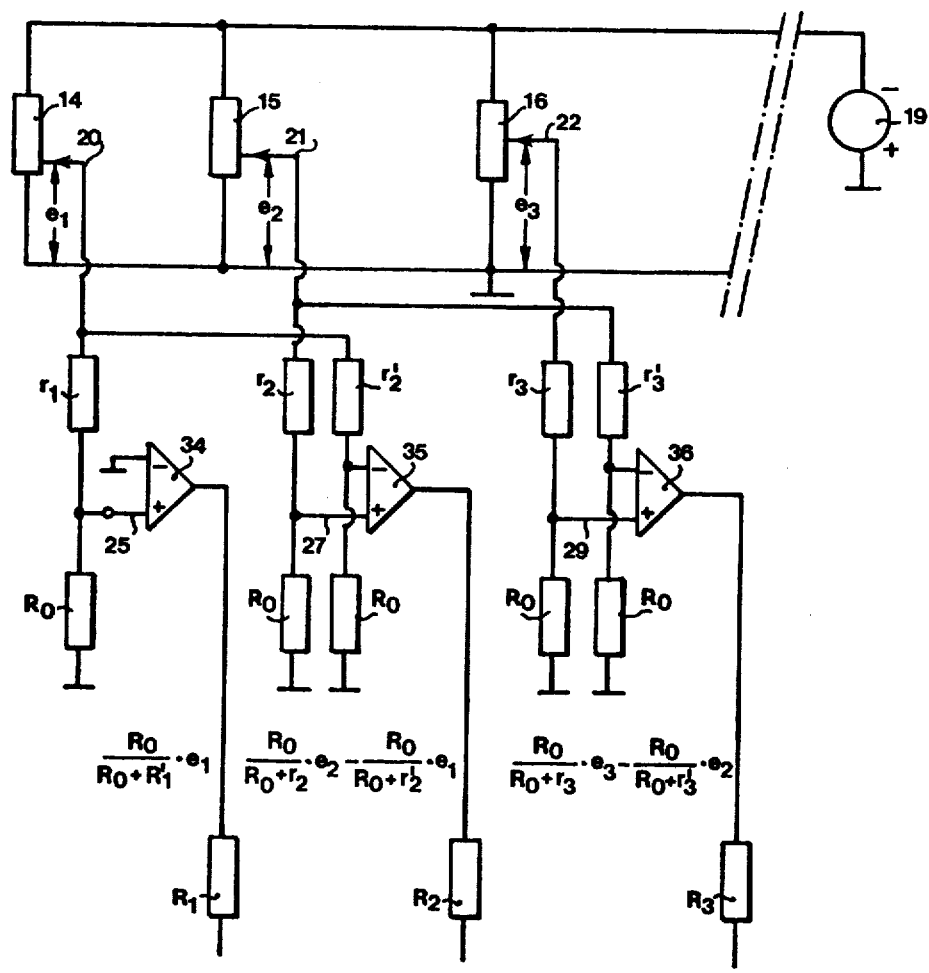
Figure 9:
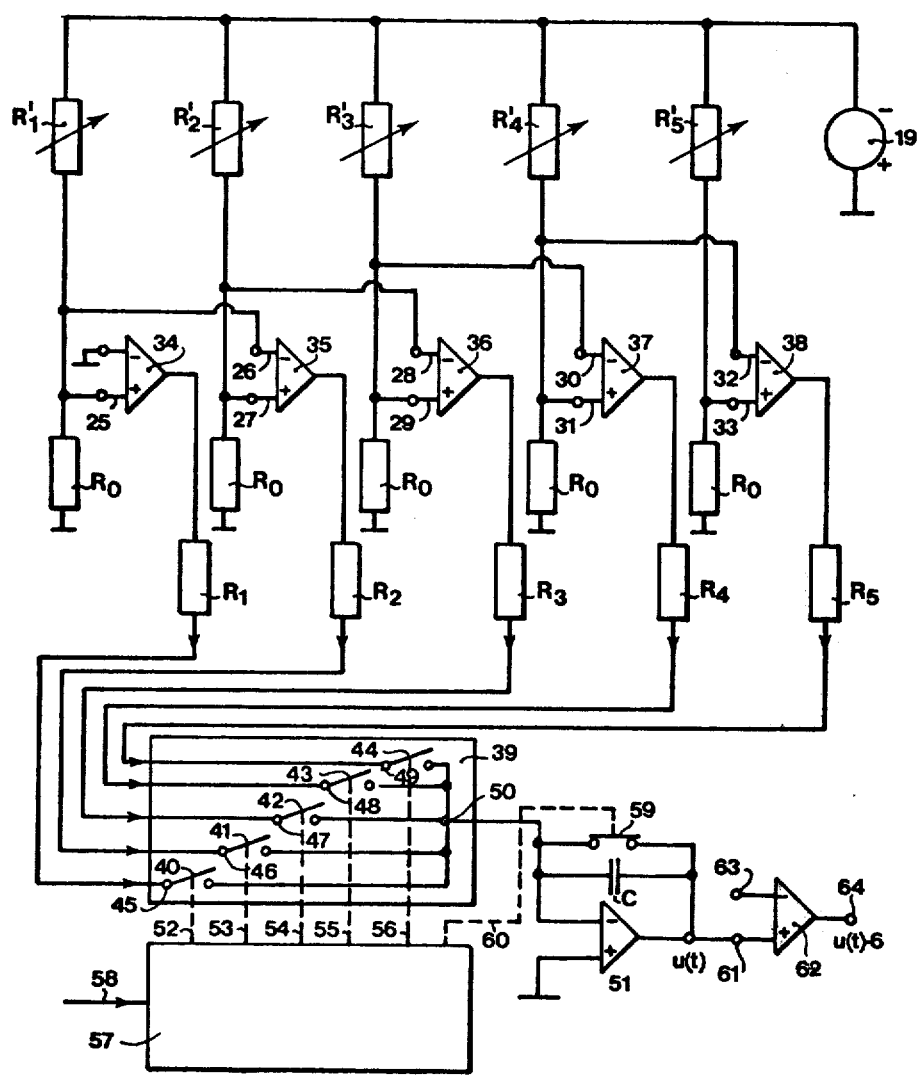

In the embodiment shown in FIG. 9 use is made of variable resistors $R_1'$ to $R_5'$ instead of the potentiometers used in the control voltage generator according to FIGS. 2, 7 and 8. The voltage sources supplying the voltages to the inputs of the differential amplifiers 34 to 38 may now be considered to be made up of the d.c. voltage source 19 and voltage dividers $R_0/R'$. For example, the voltage $e_1$ at the input 25 of differential amplifier 34 is obtained from a voltage divider consisting of the variable resistor $R_1'$ and the resistor $R_0$. The voltage $u(t_1)$ is given by $$\begin{aligned} u(t_1) &= \frac{-1}{R_1 C} \int_0^{t_1} \frac{R_0}{R_0 + R_1'} \cdot E \, dt \\ &= \frac{-t_1}{R_1 C} \cdot \frac{R_0}{R_0 + R_1'} \cdot E \end{aligned} \qquad (22)$$

where E = voltage of voltage source 19.
The voltage $u(t_2)$ is given by $$u(t_2) = \frac{-1}{R_2 C} \int_{t_1}^{t_2} (\frac{R_0}{R_0 + R_2'} \cdot E - \qquad (23)$$

$$\frac{R_0}{R_0 + R_1'} \cdot E)dt + u(t_1) = \frac{-(t_2 - t_1)}{R_2C} \left( \frac{R_0}{R_0 + R_2'} \cdot E - \frac{R_0}{R_0 + R_1'} \cdot E \right) - \frac{t_1}{R_1C} \cdot \frac{R_0}{R_0 + R_1'} \cdot E$$

For $u(t_2)$ to be only dependent on $R_2'$ and independent from $R_1'$ the following relation should be satisfied $$\frac{t_2 - t_1}{R_2C} = \frac{t_1}{R_1C} \tag{24}$$

In that case $$u(t_2) = \frac{-(t_2 - t_1)}{R_2C} \cdot \frac{R_0}{R_0 + R_2'} \cdot E \tag{25}$$

If the relation (18) holds, then $$u(t_1) = \frac{-R_0}{R_0 + R_1'} \cdot E \tag{26}$$

$$u(t_2) = \frac{-R_0}{R_0 + R_2'} \cdot E$$

$$u(t_3) = \frac{-R_0}{R_0 + R_3'} \cdot E$$

$$u(t_4) = \frac{-R_0}{R_0 + R_4'} \cdot E$$

$$u(t_5) = \frac{-R_0}{R_0 + R_5'} \cdot E$$

It is seen from (22), (25) and (26) that although any voltage u(t) may only be varied by adjusting the respective resistor, and is not influenced by the settings of the other variable resistors, it is not linearly related to the setting of the corresponding resistor. In this respect the use of potentiometers as in the embodiments shown in FIGS. 2, 7 and 8 is to be preferred, in the case where a linear relation is desired.

Further variant embodiments are shown in FIGS. 10-14. These are characterized by the use of a single differential amplifier 89, common for all voltages $e_1$ to $e_5$.

In FIG. 10 the inputs 90, 91 of differential amplifier 89 are connected to switching units 92 and 93 respectively. These switching units are identical with the switching unit 39 and each comprise 5 electronic switches 94 to 98 and 99 to 103, respectively. All switches in closed state, have internal resistances which are negligible with respct to those of resistors $R_1$ to $R_5$. Switches 94 to 98 have their right hand contacts commonly connected to the input 90 of the common differential amplifier 89. Likewise, the left hand contacts of switches 99 to 103 are commonly connected to the other input 91 of the differential amplifier 89. The other contacts of the switches are connected to sliding contacts 20-24. The switches 94 to 98 and 99 to 103 are controlled by timing generator 57 as indicated by the dash lines 52 to 56. At the start of the transmission-reception period ($t=0$) the switch 59 is opened and the switching units 39, 92 and 93 will under the control of timing generator 57 close switches 40, 94 and 99, respectively for a time interval $t_1$. As a result, the integrator 51 is set into operation for a first time interval 0 to $t_1$ to integrate output voltage $e_1$ of the differential amplifier 89.

At time $t_1$ the timing generator 57 closes the switches 41, 95 and 100, whereupon the common differential amplifier 89 forms the difference voltage $e_2-e_1$, which is integrated for a time interval $t_1$ to $t_2$ by integrator 51. Likewise, the control voltages u(t) are obtained in the remaining intervals $t_2$ to $t_3$, $t_3$ to $t_4$ and $t_4$ to $t_5$.

Figure 12:
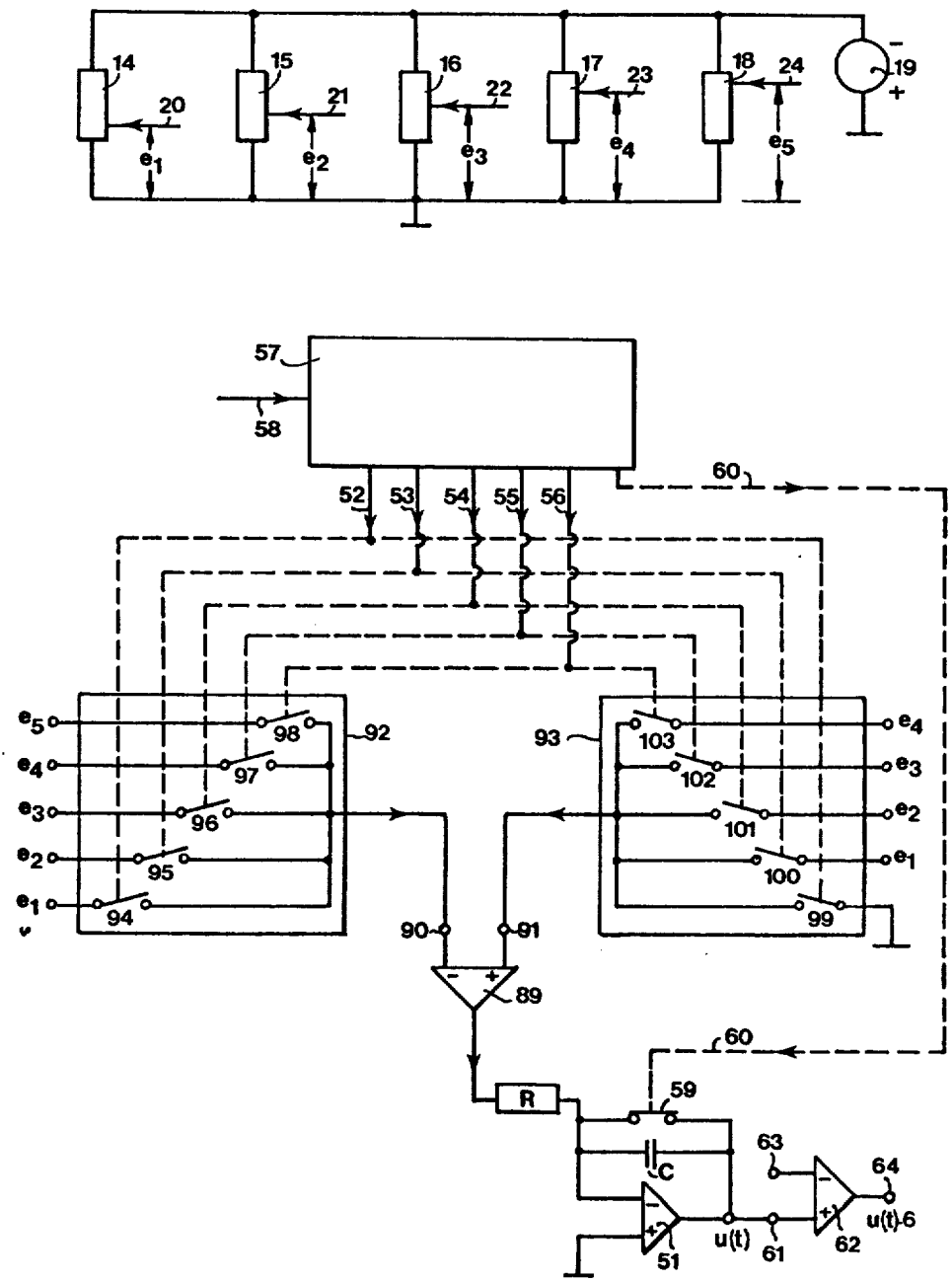
Figure 13:
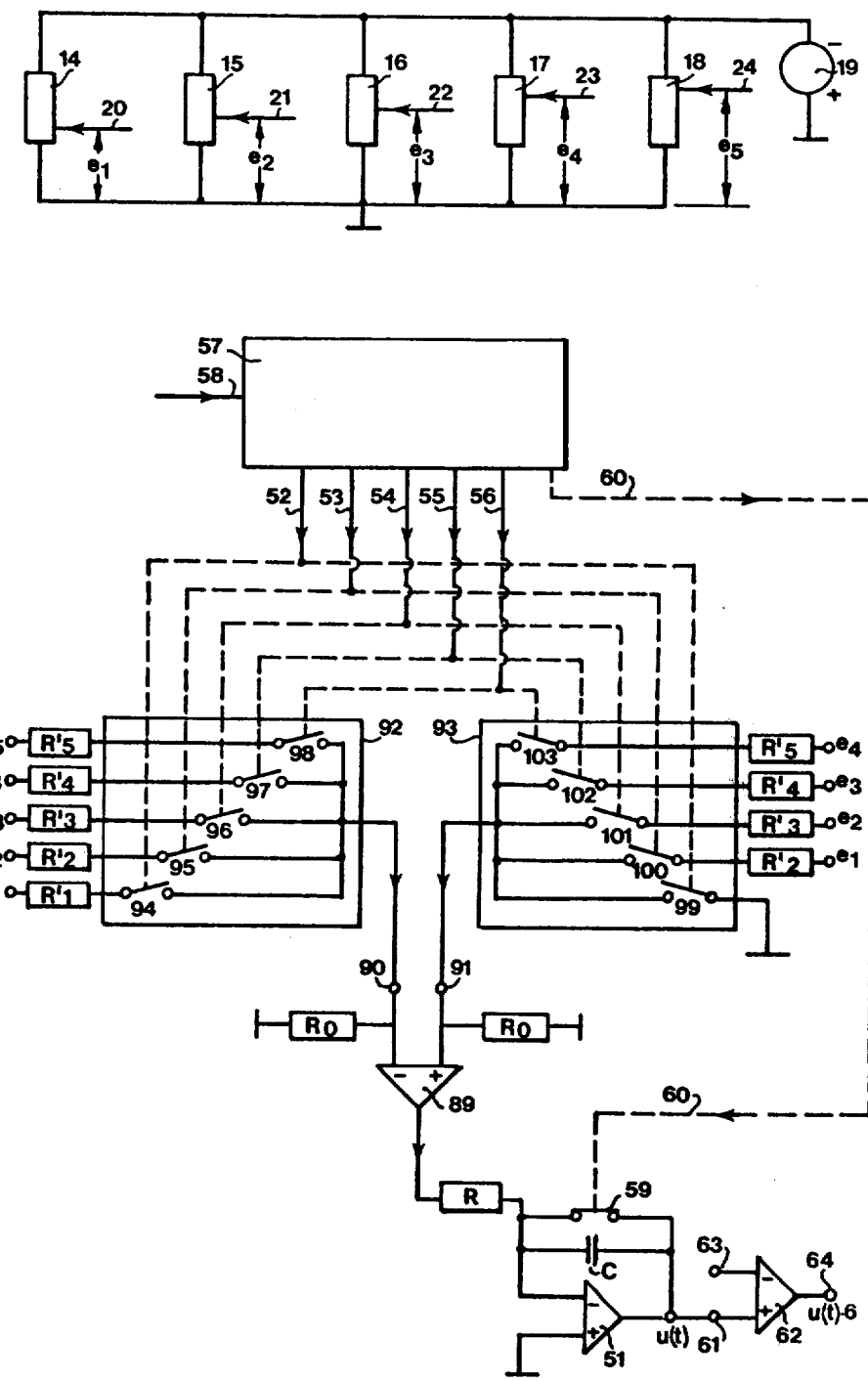

The embodiment according to FIG. 11 only differs from that of FIG. 10 in that with the former the switching unit 39 and the integrator 51 are interconnected via the resistors $R_1$ to $R_5$. FIG. 12 shows a simplified embodiment which also is provided with a common differential amplifier 89 and, moreover, with a common resistor R for the integrator 51. With this control voltage use is made of equally long time intervals ($t_1=t_2-t_1=t_3-t_2=t_4-t_3=t_5-t_4$). In that case no switching unit 39 is needed. Like the embodiment according to FIG. 12 the one shown in FIG. 13 has a common differential amplifier 89 and a common resistor R, but the latter differs from the former in that the voltage sources not only comprise a voltage source 19 and potentiometers 14 to 18, but also voltage dividers $R_1'/R_0$; $R_2'/R_0$; $R_3'/R_0$; $R_4'/R_0$ and $R_5'/R_0$.

The control voltage $u(t_1)$ is now given by $$u(t_1) = \frac{-1}{RC} \int_0^{t_1} \frac{R_0}{R_0 + R_1'} \cdot e_1 \, dt = \frac{-t_1}{RC} \cdot \frac{R_0}{R_0 + R_1'} \cdot e_1 \tag{27}$$

The resistance values $R_0$ and $R_1'$ are now so chosen that $$\frac{R_0}{R_0 + R_1'} = \frac{1}{t_1} \tag{28}$$

so that $$u(t_1) = \frac{-e_1}{RC} \tag{29}$$

The control voltage $u(t_2)$ follows from $$u(t_2) = \frac{-1}{RC} \int_{t_1}^{t_2} \left( \frac{R_0}{R_0 + R_2'} \cdot e_2 - \frac{R_0}{R_0 + R_2'} \cdot e_1 \right) dt + u(t_1) = \tag{30}$$

$$\frac{-(t_2 - t_1)}{RC} \cdot \frac{R_0}{R_0 + R_2'} (e_2 - e_1) - \frac{e_1}{RC}$$

The resistance value $R_2'$ is so chosen that $$\frac{R_0}{R_0 + R_2'} = \frac{1}{t_2 - t_1} \tag{31}$$

so that $$u(t_2) = \frac{-e_2}{RC} \tag{32}$$

Likewise the other resistance values $R_3'$, $R_4'$ and $R_5'$ are so chosen that $$\frac{R_0}{R_0 + R_3'} = \frac{1}{t_3 - t_2} \tag{33}$$

$$\frac{R_0}{R_0 + R_4'} = \frac{1}{t_4 - t_3} \tag{34}$$

$$\frac{R_0}{R_0 + R_5'} = \frac{1}{t_5 - t_4} \tag{35}$$

whereby $$u(t_3) = \frac{-e_3}{RC} \tag{36}$$

-continued $$u(t_4) = \frac{-e_4}{RC} \tag{37}$$

$$u(t_5) = \frac{-e_5}{RC} \tag{38}$$

By choosing the resistance values $R_0$ and $R_1'$ such that $$\frac{R_0}{R_0 + R_1'} = \frac{RC}{t_1}$$
$$\frac{R_0}{R_0 + R_2'} = \frac{RC}{t_2 - t_1}$$
$$\frac{R_0}{R_0 + R_3'} = \frac{RC}{t_3 - t_2} \tag{39}$$
$$\frac{R_0}{R_0 + R_4'} = \frac{RC}{t_4 - t_3}$$
$$\frac{R_0}{R_0 + R_5'} = \frac{RC}{t_5 - t_4}$$

the control voltages u(t) are $$\begin{aligned} u(t_1) &= -e_1 \\ u(t_2) &= -e_2 \\ u(t_3) &= -e_3 \\ u(t_4) &= -e_4, \text{ and} \\ u(t_5) &= -e_5 \end{aligned} \tag{40}$$

Figure 14:
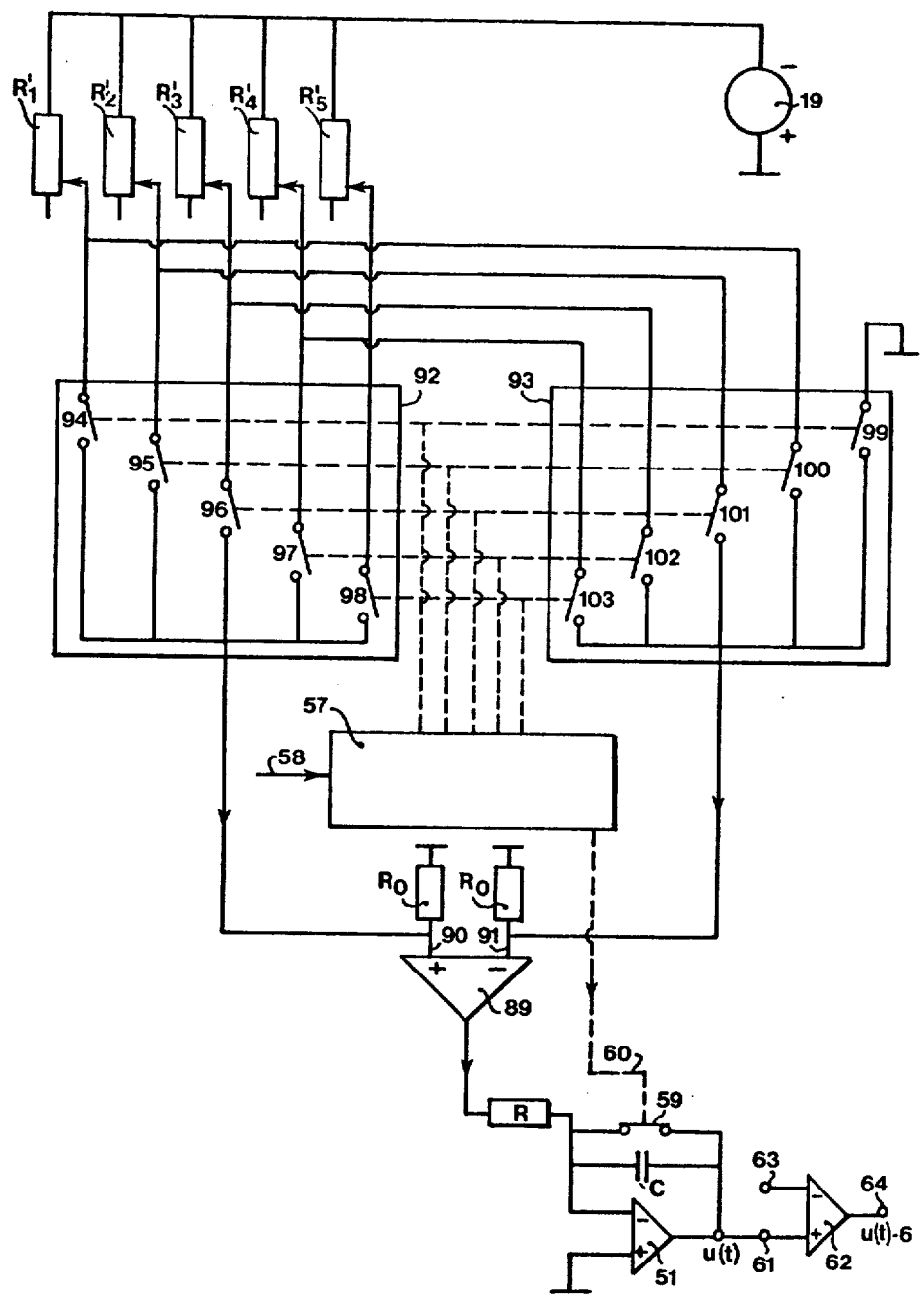

In the control voltage generator shown in FIG. 14 the potentiometers 14 to 18 have been replaced by variable resistors $R_1'$ to $R_5'$. These resistors form voltage dividers with the resistors $R_0$ connected to the inputs 90, 91 of common differential amplifier 89.

The control voltage $u(t_1)$ is $$u(t_1) = \frac{-1}{RC} \int_0^{t_1} \frac{R_0}{R_0 + R_1'} \cdot E \, dt = \tag{40}$$
$$\frac{-t_1}{RC} \cdot \frac{R_0}{R_0 + R_1'} \cdot E$$

where E = voltage of voltage source 19.
The voltage $u(t_2)$ is $$u(t_2) = \frac{-1}{RC} \int_{t_1}^{t_2} (\frac{R_0}{R_0 + R_2'} \cdot E - \tag{42}$$
$$\frac{R_0}{R_0 + R_1'} \cdot E) \, dt + u(t_1) =$$
$$\frac{-(t_2 - t_1)}{RC} \cdot (\frac{R_0}{R_0 + R_2'} - \frac{R_0}{R_0 + R_1'}) \cdot E -$$
$$\frac{t_1}{RC} \cdot \frac{R_0}{R_0 + R_1'} \cdot E$$

By choosing for equal time intervals, i.e., for $$t_5 - t_4 = t_4 - t_3 = t_2 - t_1 = t_1 = t \tag{43}$$

it follows $$u(t_2) = \frac{-t}{RC} \cdot \frac{R_0}{R_0 + R_2'} \cdot E \tag{44}$$

$$u(t_3) = \frac{-t}{RC} \cdot \frac{R_0}{R_0 + R_3'} \cdot E \tag{45}$$

$$u(t_4) = \frac{-t}{RC} \cdot \frac{R_0}{R_0 + R_4'} \cdot E \tag{46}$$

$$u(t_5) = \frac{-t}{RC} \cdot \frac{R_0}{R_0 + R_5'} \cdot E \tag{47}$$

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

What is claimed as new and desired to be protected by Letters Patent is set forth in the appended claims:

1. In an echoscope for examination of objects with the aid of an ultrasound beam, comprising at least one electro-acoustic element for transmitting and receiving ultrasonic pulses during a transmission-reception period; an amplifier with time-dependent gain control co-operating with the electro-acoustic element for amplifying the echo signals supplied by said element; a control voltage generator connected to said amplifier for supplying a control voltage thereto to determine the signal gain as a function of time; adjusting means in said control voltage generator for permitting changing the magnitude of the control voltage as a function of time in n consecutive time intervals of the transmission-reception period, which are bounded by the interval points of time $t_0, t_1, t_2 \ldots, t_i, t_j, t_k, \ldots, t_{n-1}, t_n$; and a display connected to the echo signal amplifier for the visual display of the echo signals received during each transmission-reception period, the improvement of the control voltage generator comprising a. at least two adjustable voltage sources, each of which cooperates with the adjusting means for arbitrarily setting the voltages ($e_i$, $e_j$) of said sources prevailing at the corresponding interval points of time ($t_i$ and $t_j$ respectively) between a minimum and a maximum value;

b. at least one differential amplifier co-operating with the adjustable voltage sources for providing a difference voltage ($a_j e_j - b_j e_i$) during a time interval $t_i$ to $t_j$, $a_j$ and $b_j$ being multiplication factors representing a possible attenuation or amplification of the voltages ($e_i$, $e_j$) before their being supplied to the differential amplifier;

c. integrator means for supplying the control voltage to the echo signal amplifier, said integrator means co-operating with the differential amplifier to integrate the difference voltage ($a_j e_j - b_j e_i$) during the respective time interval ($t_i$ to $t_j$) with an integrator time constant $(RC)_j$; and d. switching means co-operating with said integrator means for successively integrating the difference voltages ($a_j e_j - b_j e_i$) during consecutive time intervals ($t_j - t_i$), said time intervals ($t_j - t_i$) corresponding to the respective integrator time constants $(RC)_j$ according to the relation $$b_k \cdot \frac{t_k - t_j}{(RC)_k} = a_j \cdot \frac{t_j - t_i}{(RC)_j}$$

with $i = 0, 1, 2, \ldots, n-1$ $j = i+1$, and $k = j+1$, but $k \leq n$.

2. An echoscope according to claim 1, wherein said voltage sources comprise potentiometers with linear reading scales and a source of D.C. voltage connected to said potentiometers.

3. An echoscope according to claim 2, wherein said potentiometers are sliding potentiometers, having juxtaposed adjusting knobs which are slidable in substantially parallel directions, so that their positions give a picture of the signal gain as a function of time.

4. An echoscope according to claim 1, wherein said voltage sources comprise a voltage divider having a variable resistor with linear reading scale and a source of D.C. voltage connected to said voltage divider.

5. An echoscope according to claim 4, wherein said resistors are sliding resistors having juxtaposed adjusting knobs which are slidable in substantially parallel directions, so that their positions give a picture of the signal gain as a function of time.

6. An echoscope according to claim 1, wherein said echo signal amplifier comprises an electronic amplifier with a variable resistor for setting the gain connected to said amplifier, said resistor having means for electrically setting the resistance value, and being connected to the output of said control voltage generator.

7. An echoscope according to claim 6, wherein said resistor is an electronic resistor.

8. An echoscope according to claim 7, wherein said electronic resistor is a field-effect transistor.

9. An echoscope according to claim 6, wherein said electronic amplifier is a wideband video amplifier with differential input and outut.

10. An echoscope according to claim 1, wherein the control voltage generator is provided with
  a. n voltage sources, one for each interval point of time ($\ldots, t_i, t_j, t_k, \ldots t_{n-1}, t_n$);
  b. n differential amplifiers each of which is connected to two of said voltage sources;
  c. common integrator means cooperating with the differential amplifiers to integrate their output voltages ($\ldots; e_j - e_i; \ldots; e_n - e_{n-1}$) during the corresponding time intervals ($\ldots; t_i$ to $t_j; \ldots; t_{n-1}$ to $t_n$); and
  d. switching means cooperating with said common integrator means for successively connecting the outputs of the differential amplifiers to the input of the integrator means during the corresponding time intervals ($\ldots; t_i$ to $t_j; \ldots; t_{n-1}$ to $t_n$).

11. An echoscope according to claim 10, wherein said switching means comprises a switching unit provided with a number of switches, one contact of each of said switches being connected to the output of one of said differential amplifiers, the other contact of each of said switches being connected to the input of the integrator means, and timing generator means cooperating with the switching unit to successively close the switches at the interval points of time.

12. An echoscope according to claim 1, wherein the control voltage generator is provided with
  a. n voltage sources, one for each interval point of time ($\ldots, t_i, t_j, t_k, \ldots, t_{n-1}, t_n$);
  b. a single differential amplifier common for all voltage sources;
  c. switching means co-operating with said common differential amplifier for successively connecting the voltages ($e_i, e_j$) of the voltage sources to the inputs of said common differential amplifier during the corresponding time interval ($t_i$ to $t_j$); and
  d. common integrator means co-operating with the common differential amplifier to integrate the output voltage ($e_1 - e_0; e_2 - e_1; \ldots; e_j - e_i; \ldots; e_n - e_{n-1}$) during the corresponding time interval (0 to $t_1; t_1$ to $t_2; \ldots; t_i$ to $t_j; \ldots; t_{n-1}$ to $t_n$).

13. An echoscope according to claim 12, wherein said switching means comprises a switching unit for each input of said common differential amplifier, said switching unit being provided with switches to supply the voltages of the voltage sources to an input of the common differential amplifier, and timing generator means co-operating with the switching unit to successively close the switches at the interval points of time ($t_i, t_j$).

14. An echoscope according to claim 1 wherein said switching means comprises electronic switches.

15. An echoscope according to claim 1, wherein said time intervals ($t_j - t_i$) correspond to the respective integrator time constants (RC)$_j$ according to the relation $$\ldots \cdot a_k \cdot \frac{t_k - t_j}{(RC)_k} = a_j \cdot \frac{t_j - t_i}{(RC)_j} = \ldots = a_1 \cdot \frac{t_1 - t_0}{(RC)_1}$$

16. An echoscope according to claim 1, wherein said time intervals ($t_j - t_i$) correspond to the respective integrator time constants (RC)$_j$ acccording to the relation $$\ldots \frac{t_k - t_j}{(RC)_k} = \frac{t_j - t_i}{(RC)_j} = \ldots = \frac{t_2 - t_1}{(RC)_2} = \frac{t_1 - t_0}{(RC)_1}$$

17. An echoscope according to claim 16, wherein the respective integrator time constants are equal, so that $$\ldots t_k - t_j = t_j - t_i = \ldots = t_2 - t_1 = t_1 - t_0.$$

18. In an echoscope for examination of parts inside a human body with the aid of ultrasonic pulses, comprising an ultrasonic transducer to be externally placed on the body of a patient; a number of electro-acoustic elements supported in said transducer for transmitting and receiving ultrasonic pulses during each transmission-reception period into and from the body, respectively, said transmitting elements having parallel axes of radiation lying in a plane adapted to intersect the body part being examined along a predetermined cross-section; an amplifier with time-dependent gain control cooperating with the electro-acoustic elements for amplifying the echo signals supplied by the receiving elements; a control voltage generator connected to said amplifier for supplying a control voltage thereto to determine the signal gain as a function of time; adjusting means in said control voltage generator for permitting changing the magnitude of the control voltage as a function of time in n consecutive time intervals of the transmission-reception period, which are bounded by the interval points of time $t_0, t_1, t_2, \ldots, t_i, t_j, t_k, \ldots, t_{n-1}, t_n$; a cathode ray tube including a screen co-operating with the echo signal amplifier; means for displaying echo signals reflected by parts of the body at the predetermined cross-section and received by said elements on the screen of said cathode ray tube in a cartesian coordinate system wherein one coordinate represents the position of the transmitted ultrasound beam, and another coordinate represents the time of reception of said echo signals; and means for repeatedly exciting said electro-acoustic elements at such a repetition frequency that an instantaneous image of said cross-section is displayed on the screen of said cathode ray tube, the improvement of the control voltage generator being provided with (a) at least two adjustable voltage sources, each of which cooperates with one of the adjusting means for arbitrarily setting the voltages ($e_i, e_j$) of said sources prevailing at the corresponding interval points of time ($t_i$ and $t_j$ respectively) between a minimum and a maximum value; (b) at least one differential amplifier co-operating with the adjustable voltage sources for providing a difference voltage ($a_j e_j - b_j e_i$) during a time interval $t_i$ to $t_j$, $a_j$ and $b_j$ being multiplication factors representing a possible attenuation or amplification of the voltages ($e_i$, $e_j$) before their being supplied to the differential amplifier; (c) integrator means for supplying the control voltage to the echo signal amplifier, said integrator means cooperating with the differential amplifier to integrate the difference voltage ($a_je_j - b_je_i$) during the respective time interval ($t_i$ to $t_j$) with an integrator time constant $(RC)_j$; and (d) switching means cooperating with said integrator means for successively integrating the difference voltages ($a_je_j - b_je_i$) during consecutive time intervals ($t_j - t_i$), said time intervals ($t_j - t_i$) corresponding to the respective integrator time constant $(RC)_j$ according to the relation $$b_k \cdot \frac{t_k - t_j}{(RC)_k} \quad a_j \cdot \frac{t_j - t_i}{(RC)_j}$$

with $i = 0, 1, 2, 3, \ldots, n-1$; $j = i+1$ and $k = j+1$ but $k \leq n$.

19. An echoscope according to claim 18, wherein said voltage sources comprise potentiometers with linear reading scales and a source of D.C. voltage connected to said potentiometers.

20. An echoscope according to claim 19, wherein said potentiometers are sliding potentiometers, having a juxtaposed adjusting knobs which are slidable in substantially parallel directions, so that their positions give a picture of the signal gain as a function of time.

21. An echoscope according to claim 18, wherein said voltage sources comprise a voltage divider having a variable resistor with linear reading scale and a source of D.C. voltage connected to said voltage divider.

22. An echoscope according to claim 21, wherein said resistors are sliding resistors having juxtaposed adjusting knobs which are slidable in substantially parallel directions, so that their positions give a picture of the signal gain as a function of time.

23. An echoscope according to claim 18, wherein said echo signal amplifier comprises an electronic amplifier with a variable resistor for setting the gain connected to said amplifier, said resistor having means for electrically setting the resistance value, and being connected to the output of said control voltage generator.

24. An echoscope according to claim 23, wherein said resistor is an electronic resistor.

25. An echoscope according to claim 24, wherein said electronic resistor is a field-effect transistor.

26. An echoscope according to claim 23, wherein said electronic amplifier is a wideband video amplifier with differential input and output.

27. An echoscope according to claim 18, wherein the control voltage generator is provided with
   a. n voltage sources, one for each interval point of time ($\ldots, t_i, T_j, T_k, \ldots t_{n-1}, t_n$);
   b. n differential amplifiers each of which is connected to one of said voltage sources;
   c. common integrator means cooperating with the differential amplifiers to integrate their output voltages ($\ldots; e_j - e_i; \ldots; e_n - e_{n-1}$) during the corresponding time intervals ($\ldots t_i$ to $t_j; \ldots; t_{n-1}$ to $t$); and
   d. switching means cooperating with said common integrator means for successively connecting the outputs of the differential amplifiers to the input of the integrator means during the corresponding time intervals ($\ldots; t_i$ to $t_j; t_{n-1}$ to $t_n$).

28. An echoscope according to claim 27, wherein said switching mean comprises a switching unit provided with a number of switches, one contact of each of said switches being connected to the output of one of said differential amplifiers, the other contact of each of said switches being connected to the input of the integrator means and timing generator means cooperating with the switching unit to succesively close the switches at the interval points of time.

29. An echoscope according to claim 18, wherein the control voltage generator is provided with
   a. n voltage sources, one for each interval point of time ($\ldots, t_i, t_j, t_k, \ldots, t_{n-1}, t_n$),
   b. a single differential amplifier common for all voltage sources;
   c. switching means co-operating with said common differential amplifier for successively connecting the voltages ($e_i, e_j$) of the voltage sources to the inputs of said common differential amplifier during the corresponding time interval ($t_i$ to $t_j$) and
   d. common integrator means co-operating with the common differential amplifier to integrate the output voltage ($e_1 - e_0; e_2 - e_1; \ldots; e_j - e_i; \ldots; e_n - e_{n-1}$) during the corresponding time interval (0 to $t_1$; $t_1$ to $t_2$; $\ldots$; $t_i$ to $t_j$; $\ldots$; $t_{n-1}$ to $t_n$).

30. An echoscope according to claim 29, wherein said switching means comprises a switching unit for each input of said common differential amplifier, said switching unit being provided with switches to supply the voltages of the voltage sources to an input of th common differential amplifier, and timing generator means co-operating with the switching unit to successively close the switches at the interval points of time ($t_i, t_j$).

31. An echoscope according to claim 18 wherein said switching means comprises electronic switches.

* * * * *